(12) United States Patent
Lin et al.

(10) Patent No.: US 6,693,444 B2
(45) Date of Patent: Feb. 17, 2004

(54) CIRCUIT DESIGN FOR LIQUID PROPERTY SENSOR

(75) Inventors: Yingjie Lin, El Paso, TX (US); Su-Chee Simon Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 32 days.

(21) Appl. No.: 10/199,651

(22) Filed: Jul. 19, 2002

(65) Prior Publication Data
US 2004/0012399 A1 Jan. 22, 2004

(51) Int. Cl.[7] ............................................... G01R 27/08
(52) U.S. Cl. ...................................... 324/698; 324/664
(58) Field of Search ................................. 324/698, 664

(56) References Cited

U.S. PATENT DOCUMENTS

| | | | |
|---|---|---|---|
| 4,885,529 A | * | 12/1989 | Lee et al. ..................... 324/663 |
| 5,068,617 A | * | 11/1991 | Reich .......................... 324/663 |
| 6,318,152 B1 | * | 11/2001 | Hagihara et al. ........... 73/35.02 |
| 6,519,539 B1 | * | 2/2003 | Freeman et al. ............... 702/65 |
| 6,578,416 B1 | * | 6/2003 | Vogel et al. ................ 73/304 C |
| 2001/0020383 A1 | * | 9/2001 | Moos et al. ................. 73/31.06 |
| 2003/0057968 A1 | * | 3/2003 | Wang et al. ................. 324/690 |

* cited by examiner

Primary Examiner—Charles H. Nolan, Jr.
(74) Attorney, Agent, or Firm—Jimmy L. Funke

(57) ABSTRACT

An apparatus for measuring the complex impedance of a fuel includes a sensing element in contact with the fuel. The sensing element is excited with an excitation signal of a predetermined frequency, preferably in a range of 10 kHz to 100 kHz. The induced signal is used to generate a phase and a magnitude signal indicative of the phase and magnitude of the complex impedance. From the phase and magnitude signals, the resistance and capacitance of the fuel can be calculated. Correction for variations in temperature of the electronics is provided, as is variable control to adjust the resolution of the magnitude signal required by fuels of varying content, such as varying ethanol content.

20 Claims, 2 Drawing Sheets

CIRCUIT DESIGN FOR LIQUID PROPERTY SENSOR

TECHNICAL FIELD

The invention relates in general to sensors used to detect properties of a fuel and, more particularly, to a sensor for detecting the complex impedance of a fuel.

BACKGROUND OF THE INVENTION

The property of a gasoline, such as its conductivity or dielectric constant, are often important for operation of a motor vehicle. Such constants can be used to provide the concentration of ethanol in a gasoline and can also determine the amount of water mixed in with the fuel. For example, experimental data shows that the fuel dielectric constant is directly proportional to the ethanol concentration but relatively insensitive to water contamination, while fuel conductivity is very sensitive to water concentration. Thus, for these applications and others, there is a need for a fuel sensor that precisely measures the impedance of fuel.

Current sensor designs have problems handling small capacitance measurements, requiring a relatively large sensing element to increase the signal-to-noise ratio. Further, instead of separately measuring resistance and capacitance, the designs measure total impedance, requiring a relatively high frequency in the 10–100 MHz range to reduce the conductivity impact. Two excitation frequencies are then needed to complete the measurement, low frequency for resistance measurements and high frequency for capacitance measurements.

SUMMARY OF THE INVENTION

The present invention is a sensor design with a small sensing element to minimize sensor package size, which is capable of measuring both resistance and capacitance using a single, low excitation frequency. The low excitation frequency reduces circuit radiation and, hopefully, the cost of components. The sensor is capable of handling very small capacitance and resistance values with high accuracy.

Specifically, the apparatus for determining the complex impedance of a fuel includes a sensing element in contact with the fuel, means for exciting the sensing element with an excitation signal of a predetermined frequency to generate an induced signal, means for generating a phase signal using the induced signal, and means for producing a magnitude signal using the induced signal. The phase signal is indicative of the phase of the complex impedance, while the magnitude signal is indicative of the magnitude of the complex impedance. The apparatus can include means, such as a microcontroller, for calculating either the resistance or the capacitance or both using the magnitude signal and the phase signal. The engine controller can receive the magnitude signal and the phase signal and calculate these quantities.

A typical sensing element comprises two spaced electrodes. Preferably, one or more direct current (DC) block capacitors remove DC components from the excitation signal and the induced signal.

The excitation signal is generally a sinusoidal voltage supplied by a sinusoidal source. Preferably, the predetermined frequency of the excitation signal is in a range of 10 kHz to 100 kHz. The signal induced by the sensing element is an induced current signal, which is preferably converted to an induced voltage signal by a current-to-voltage converter. In a preferred embodiment, the current-to-voltage converter includes an operational amplifier with an adjustable gain. The adjustable gain is then used to change the resolution of the induced voltage signal based upon the resolution of the magnitude signal. If the signal resolution is not high enough, the gain can be adjusted. The adjustable gain can include a plurality of selectable impedances. Then, one embodiment of the invention can include means for selecting at least one of the plurality of selectable impedances to change a resolution of the induced voltage signal based upon a resolution of the magnitude signal. This selection can be performed by, for example, a microcontroller or the engine controller.

The means for generating the phase signal can include means for comparing the induced signal to the excitation signal the phase signal. In one embodiment of the invention, this comparison the comparison means includes a first comparator for generating a first square wave corresponding to the induced signal, a second comparator for generating a second square wave corresponding to the excitation signal and a pulse width modulator for comparing the first square wave and the second square wave and generating the phase signal. The phase signal thus has a duty cycle representing the phase of the complex impedance.

The means for producing the magnitude signal preferably includes some type of peak detector. The illustrated embodiment describes a full-wave rectifier for receiving the induced signal and producing a rectified signal and a low pass filter coupled to the full-wave rectifier for receiving the rectified signal and producing the magnitude signal. A differential amplifier can be coupled to the low pass filter for amplifying the magnitude signal.

One desirable embodiment includes a switch that selects a reference signal to use in the apparatus such that means for producing the magnitude signal produces a reference magnitude signal. This reference magnitude signal can be used to adjust the magnitude output for temperature variations in the sensor apparatus. More specifically, the apparatus can include means for calculating an adjustment factor, such as the microcontroller or engine controller previously mentioned. The adjustment factor represents a change in a magnitude of the reference magnitude signal from a reference voltage. This change in magnitude varies with changes in the temperature. Thus, the means for calculating the adjustment factor can adjust the magnitude signal by the adjustment factor to account for changes in ambient temperature around the electronics of the sensing apparatus.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
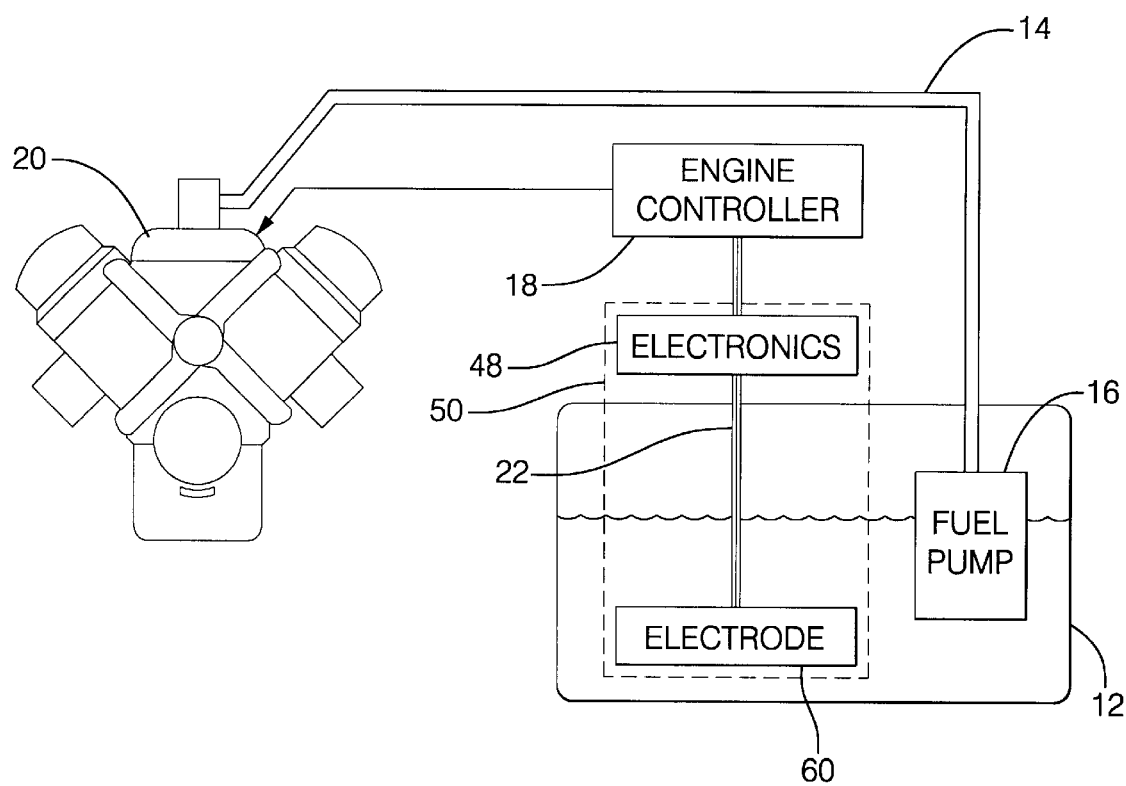
FIG. 1 is a pictorial representation of one placement of the sensor in an automobile.
Figure 2:
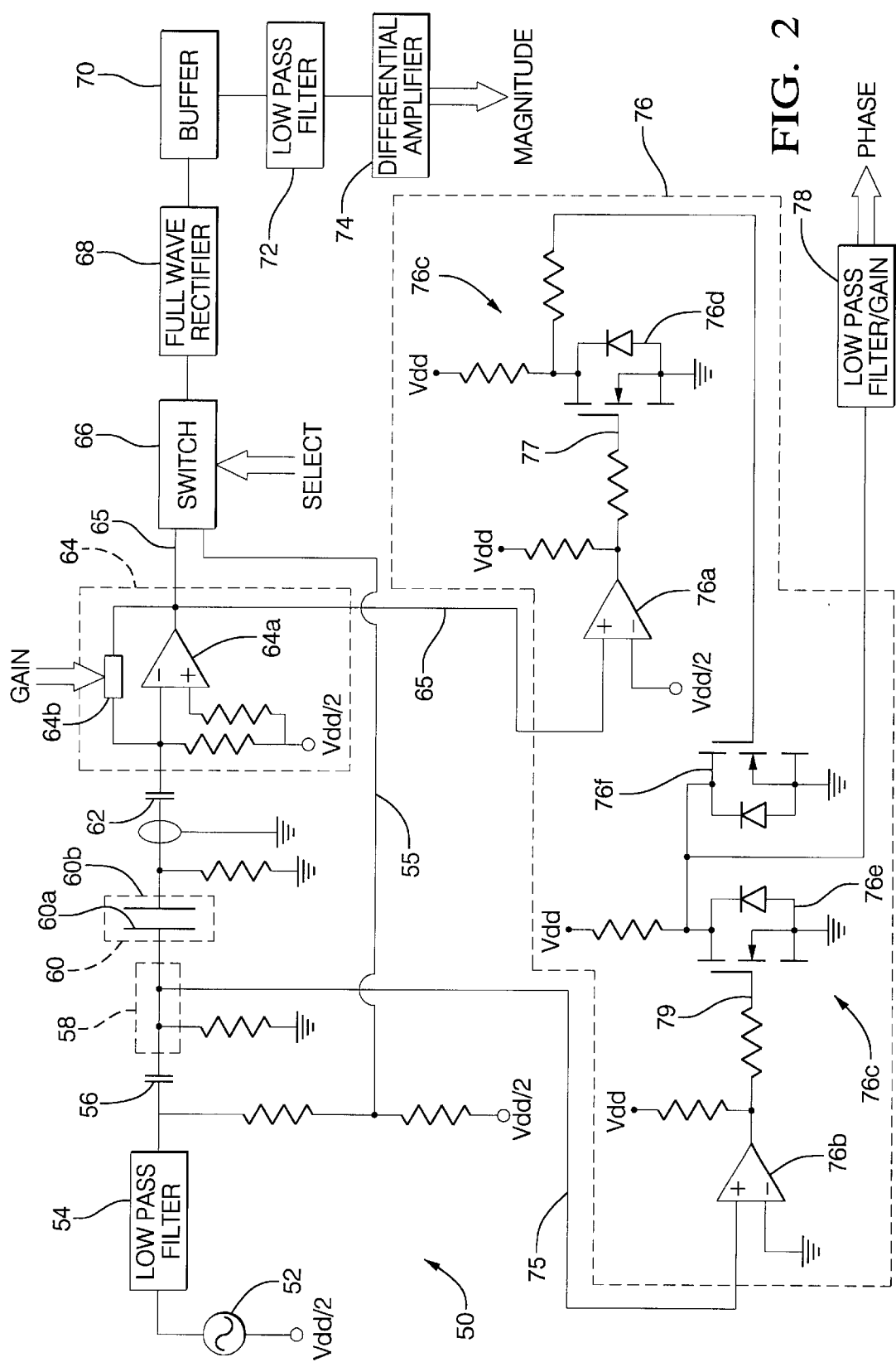
FIG. 2 shows the sensor design of the present invention.

Referring now to the drawing in detail, particularly to FIGS. 1 and 2, shown is the sensor apparatus 50 of the present invention. FIG. 1 shows the sensor apparatus 50, which includes a sensing element 60 and a control circuit or electronics 48, incorporated into an engine control system. Specifically, the sensing element 60 of the sensor apparatus 50 is located in the fuel tank 12 of a vehicle (not shown) so that it is exposed to fuel. The sensing element 60 is preferably located near the fuel pump 16, which sends fuel to the engine 20 through fuel line 14. However, the sensing element 60 can be located elsewhere where it contacts fuel, such as in the fuel line 14. The sensing element 60 is submerged in the fuel and excited, then an impedance magnitude and phase of the fuel are calculated from the induced current measured at the excitation frequency.

Specifically, the control circuit 48 of the sensor apparatus 50 excites the sensing element 60 through a shielded cable 22, such as a coaxial cable, and receives an induced signal from the sensing element 60. The control circuit 48 calculates two signals from this induced signal, one corresponding to the magnitude of the impedance and the other corresponding to the phase of the impedance. The control circuit 48 can include a standard microcontroller, like the engine controller 18, which is used in automotive applications and includes memory, input and output means and a processor. The control circuit 48 then can calculate the resistance and capacitance from the signals, supplying the these values to a diagnostic device or to the engine controller 18. Alternately, the control circuit 48 of the sensor 50 provides the magnitude and phase quantities to the engine controller 18, which performs the desired calculations. In either case, the engine controller 18 can manipulate the resistance and capacitance values to, for example, control the amount of fuel the engine 20 receives from the fuel tank 12 through the fuel line 14 relative to the intake of air for operation of an engine 20.

A block diagram of one embodiment of the sensor apparatus 50 that can perform this impedance determination is shown in FIG. 2. The sensing element 60 of the sensor 50 comprises two spaced electrodes, an excitation plate 60a and a sensing plate 60b, both made of a conductive material. The sensing element 60 is submerged in the fuel and excited by a sinusoidal wave generator 52. The sinusoidal wave generator 52 generates a sinusoidal voltage centered at the voltage Vdd/2. By example, the peak-to-peak amplitude is around 4 volts. The sinusoidal voltage is at a single frequency in the range of 10 kHz to 100 kHz. If the generator is a single stage sine wave generator 52, the voltage is first filtered through a standard low pass filter 54 to filter out high order harmonics. Alternatively, of course, a dual stage sine wave generator 52 can be used and the low pass filter 54 omitted.

The filtered voltage feeds through a voltage divider tied to Vdd/2. The resulting voltage signal provides a temperature reference voltage 55 to a switch 66. The temperature reference voltage 55, and its use with the switch 66, is discussed further herein. The filtered voltage also provides an excitation signal to the sensing element 60 through the shielded cable 22 at node 58. Specifically, the filtered voltage flows through a DC block capacitor 56, and the resulting excitation signal reaches the excitation plate, or electrode, 60a of the sensing element 60. Node 58 brings the DC voltage of the excitation plate 60a of the sensing element 60 down to ground through a grounding resistor.

The control circuit 48 receives the excitation signal from node 58 and supplies it as a reference input excitation signal 75 for a pulse width modulated (PWM) generator 76, discussed herein.

The control circuit 48 receives the current induced on the sensing element 60 from the sensing electrode 60b through the shielded cable 22. Preferably, the sensing plate, or electrode, 60b of the sensing element 60 is grounded through a resistor to bring the DC components of this induced signal to ground. Together with the ground provided for the excitation plate 60a at node 58, this ground assures that the signals supplied to the remainder of the control circuit 48 have no DC components. Also, and as shown in FIG. 2, the shield or the shielded cable 22 is preferably brought to ground, optionally through a resistor (not shown). As additional protection against DC components in the induced signal, a series-connected DC blocking capacitor 62 filters the induced signal prior to it being supplied to the inverting input of an operational amplifier (op amp) 64a configured as a current-to-voltage converter 64.

In the current-to-voltage converter 64, the inverting input of the op amp 64a is raised to Vdd/2 through a resistor, as is the non-inverting input of the op amp 64a. Feedback is supplied through a feedback impedance 64b, wherein either the reactive component or the resistive component of the feedback impedance 64b is minimized. Preferably, the feedback impedance 64b provides the op amp 64a with a variable gain such that the resolution of the output signal MAGNITUDE is adjustable by changing the feedback impedance. Ideally, the output of the converter 64 is a sinusoidal voltage centered at, for example, 2.5 volts. Depending upon the characteristics of the fuel, however, the op amp 64a can saturate, and the resolution of the signal MAGNITUDE, discussed herein, diminishes. One characteristic affecting the resolution of the signal is the ethanol content.

In the preferred embodiment, the feedback impedance 64b comprises a plurality of parallel complex impedances enabled by a gain control signal GAIN. By example, four complex impedances are connected to four outputs of a digital switch, and each complex impedance includes a large resistance value in parallel with a small capacitance value. The gain control signal GAIN is a digital signal generated by the engine controller 18 or a microcontroller (not shown) of the control electronics 48, here [0:0] to [1:1]. Whichever controller receives the output MAGNITUDE sends the signal GAIN to the digital switch, adjusting the gain of the op amp 64a until the output MAGNITUDE reaches the desired resolution. Where the fuel has a large capacitance, a small gain is desirable; where the fuel has a small capacitance, a large gain is desirable.

The output of the current-to-voltage converter 64 is a sinusoidal voltage signal 65 centered at, for example, 2.5 volts, and representative of the complex impedance of the fuel. The sinusoidal voltage signal 65, like the temperature reference voltage 55, is preferably fed into the switch 66. The switch 66 can be an analog switch, such as ADG419 from Analog Devices, Inc. of Norwood, Mass., which receives a sampling signal SELECT from the engine controller 18 or a microcontroller (not shown) of the control electronics 48. The sampling signal SELECT determines which of the sinusoidal voltage signal 65 and the temperature reference voltage 55 are used to calculate the output signal MAGNITUDE. This provides a means of correcting the output signal MAGNITUDE for temperature variations of the circuit board on which the control electronics 48 are mounted.

More specifically, the temperatures to which the sensor 50 is exposed vary significantly with operation of the vehicle in which the sensor 50 is installed. Circuit board temperatures can range, for example, from −40° C. to 125° C. Normally, the sampling signal SELECT is such that the sinusoidal voltage signal 65 passes through and is used to determine the output signal MAGNITUDE. The output signal MAGNITUDE is a DC voltage used by the controller in a lookup table, for example, to determine the impedance magnitude of the complex impedance. Testing shows, however, that signal drops for a nominal magnitude of 2 volts can be 10% or more as the temperature increases. The present invention addresses this problem by, at specific predetermined intervals, sending a sampling signal SELECT that enables the switch 66 to pass the temperature reference voltage 55 on to the remainder of the control electronics 48 that determines the output signal MAGNITUDE. This output signal MAGNITUDE is compared to the expected magnitude based upon the value of the voltage reference Vdd/2. A ratio, or adjustment factor, of the output signal MAGNITUDE developed from the temperature reference voltage 55 to the expected voltage is used to adjust the output signal MAGNITUDE based upon the sensed sinusoidal voltage signal 65. In this manner, the output signal MAGNITUDE is adjusted for temperature variation prior to using it to determine the impedance magnitude of the complex impedance.

FIG. 2 shows one circuit design that can detect the peak of the sinusoidal voltage output of the switch 66, whether it is the sensed sinusoidal voltage signal 65 or the temperature reference voltage 55. First, the signal is rectified by a standard full wave rectifier 68. After passing through a buffer 70, the signal is filtered through a low pass filter 72 to remove its AC components. The resulting DC signal is then fed through a differential amplifier 74, which sends the amplified DC signal, output signal MAGNITUDE, to a microcontroller, such as the engine controller 18. The engine controller 18 then adjusts the output signal MAGNITUDE by the last calculated adjustment factor if the output signal MAGNITUDE is based upon the sensed sinusoidal voltage signal 65, or a new adjustment factor is determined if the output signal MAGNITUDE is based upon the temperature reference voltage 55.

Optionally, the actual magnitude of the complex impedance can be determined from this voltage output signal MAGNITUDE. To do this, the engine controller 18 compares the output signal MAGNITUDE to values on a look up table determined in prior calibration experiments wherein the look up table correlates voltage outputs to impedance magnitudes. Alternately, a mathematical relationship between these two variables can be developed and used by the engine controller 18 to determine the impedance magnitude from the output signal MAGNITUDE.

The output of the current-to-voltage converter 64, which is representative of the complex impedance of the fuel, takes two paths. As described above, the sinusoidal voltage signal 65 is supplied to a peak detector, or any kind of an AC amplitude to DC converter that detects the magnitude of the peak of the signal. Second, the sinusoidal voltage signal 65 is supplied to the PWM generator 76, which compares that voltage signal 65 to the reference input excitation signal 75 to determine the phase of the complex impedance. A multitude of circuits can determine this phase from the two input signals; one is shown in FIG. 2.

The PMW generator 76 of FIG. 2 includes two comparators 76a and 76b and a pulse-width modulator circuit 76c. In the example, the sinusoidal voltage signal 65 is a sinusoidal voltage centered at 2.5 volts. It is supplied to the non-inverting input of the comparator 76a, while the inverting input of the comparator 76a is at Vdd/2. The output of the comparator 76a is a square wave 77 from 0 to 5 volts with a frequency corresponding to that of the sinusoidal voltage signal 65. The reference input excitation signal 75 is a sinusoidal voltage centered at 0 volts at the same frequency as the sinusoidal voltage signal 65. However, the sinusoidal voltage signal 65 is offset in phase from the reference input excitation signal 75, where the offset corresponds to the phase of the impedance between the node 58 and the output of the op amp 64a of the current-to-voltage converter 64. The reference input excitation signal 75, like the sinusoidal voltage signal 65, is similarly supplied to the non-inverting input of a comparator 76b, while the inverting input of the comparator 76b is at ground. The output of the comparator 76b is a square wave 79 from 0 to 5 volts with a frequency corresponding to that the reference input excitation signal 75 and with the same phase offset from the sinusoidal voltage signal 65. The two square waves 77 and 79 are provided to two field-effect transistors (FET) of a pulse-width modulator circuit 76 comprising three FETs. More specifically, each of the two square waves 77, 79 is provided as an input to the gate of a corresponding FET 76d, 76e. The source of each of the three FETs 76d–f is grounded, while the drain of each of the three FETs 76d–f is raised to Vdd through a resistive load. The output voltage at the drain of the FET 76d receiving the square wave 77 is the input voltage signal for the gate of the third FET 76f, while the output voltage of the drain of the FET 76e receiving the square wave 79 is tied to the output voltage of the drain of the third FET 76f. Thus, the output of the pulse-width modulator circuit 76c, and of the PWM generator 76, is a square wave from 0 to 5 volts with a duty cycle based upon the difference in phase, or the phase offset, of the square wave 77, representing the induced signal, and the square wave 79, representing the excitation signal.

The output of the PWM generator 76 is passed through a conventional low pass filter with a fixed gain 78. The resulting output signal PHASE is a square wave with a duty cycle ranging from 0%–50%, which is provided to the same controller as the output signal MAGNITUDE, such as the engine controller 18. The controller 18 calculates the duty cycle according to conventional methods. Through prior calibration, another look up table can be provided in the engine controller 18 whereby a duty cycle of 0%–50% corresponds to a phase of the complex impedance of 0°–180°. Once the controller 18 has the duty cycle of the output signal PHASE, it can use the look up table to determine the phase of the complex impedance. Of course, as with the calculation of the magnitude of the complex impedance, a mathematical relationship governing the relationship of the output signal PHASE to the phase of the complex impedance can be developed from the prior calibration experiments and used instead of the look up table. Given the complex output comprising the magnitude and the phase outputs, the microcontroller or engine controller 18 can determine the resistance and capacitance of the fuel by a simple calculation.

Thus is presented a sensor design can measure capacitance down to the picofarad range and measure magnitude and phase difference using a single excitation frequency in the range of 10–100 kHz. A simple calculation gives the precise measurements of resistance and capacitance.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for determining a complex impedance of a fuel, the complex impedance having a magnitude and a phase, the apparatus comprising:

a sensing element in contact with the fuel;

means for exciting the sensing element with an excitation signal of a predetermined frequency to generate an induced signal;

means for generating a phase signal using the induced signal, the phase signal indicative of the phase of the complex impedance; and means for producing a magnitude signal using the induced signal, the magnitude signal indicative of the magnitude of the complex impedance.

2. The apparatus according to claim 1, further comprising:

means for calculating at least one of a resistance and a capacitance of the fuel using the magnitude signal and the phase signal.

3. The apparatus according to claim 2 wherein the calculating means comprises:

a microcontroller receiving the magnitude signal and the phase signal.

4. The apparatus according to claim 1 wherein the sensing element comprises two spaced electrodes.

5. The apparatus according to claim 1 wherein the excitation means comprises a sinusoidal source supplying a sinusoidal voltage to the sensing element.

6. The apparatus according to claim 5 wherein the predetermined frequency is in a range of 10 kHz to 100 kHz.

7. The apparatus according to claim 1, further comprising:

a current-to-voltage converter for converting the induced signal from an induced current signal to an induced voltage signal.

8. The apparatus according to claim 7 wherein the current-to-voltage converter comprises an operational amplifier with an adjustable gain.

9. The apparatus according to claim 8 wherein the adjustable gain is adjustable to change a resolution of the induced voltage signal based upon a resolution of the magnitude signal.

10. The apparatus according to claim 9 wherein the generation means further comprises:

means for comparing the induced signal to the excitation signal to generate the phase signal.

11. The apparatus according to claim 8 wherein the adjustable gain comprises a plurality of selectable impedances.

12. The apparatus according to claim 11, further comprising:

means for selecting at least one of the plurality of selectable impedances to change a resolution of the induced voltage signal based upon a resolution of the magnitude signal.

13. The apparatus according to claim 1 wherein the generation means further comprises:

means for comparing the induced signal to the excitation signal to generate the phase signal.

14. The apparatus according to claim 13 wherein the comparison means comprises:

a first comparator for generating a first square wave corresponding to the induced signal;

a second comparator for generating a second square wave corresponding to the excitation signal; and a pulse width modulator for comparing the first square wave and the second square wave and generating the phase signal, the phase signal having a duty cycle representing the phase of the complex impedance.

15. The apparatus according to claim 1 wherein the production means comprises:

a full-wave rectifier for receiving the induced signal and producing a rectified signal; and a low pass filter coupled to the full-wave rectifier for receiving the rectified signal and producing the magnitude signal.

16. The apparatus according to claim 15 wherein the production means further comprises:

a differential amplifier coupled to the low pass filter for amplifying the magnitude signal.

17. The apparatus according to claim 1, further comprising:

a switch for selecting a reference signal wherein the production means uses the reference signal to produce a reference magnitude signal.

18. The apparatus according to claim 17, further comprising:

means for calculating an adjustment factor, the adjustment factor representing a change in a magnitude of the reference magnitude signal from a magnitude of a reference voltage.

19. The apparatus according to claim 18 wherein the means for calculating an adjustment factor further comprises means for adjusting the magnitude signal by the adjustment factor.

20. The apparatus according to claim 1 wherein the sensing element comprises two spaced electrodes and the apparatus further comprises:

at least one direct current (DC) block capacitor removing DC components from at least one of the excitation signal and the induced signal.

* * * * *